Уnited States Patent [19]

Herman

[11] Patent Number: 4,772,691

[45] Date of Patent: Sep. 20, 1988

[54] CHEMICALLY CLEAVABLE NUCLEOTIDES

[75] Inventor: Timothy M. Herman, Wauwatosa, Wis.

[73] Assignee: The Medical College of Wisconsin, Inc., Milwaukee, Wis.

[21] Appl. No.: 742,105

[22] Filed: Jun. 5, 1985

[51] Int. Cl.$^4$ .................. C07H 19/20; C07H 19/10; C07H 19/06; C07H 19/16

[52] U.S. Cl. .................................. 536/27; 536/28; 536/29; 536/23; 536/24; 536/26

[58] Field of Search .................. 536/23, 24, 26, 27, 536/28, 29

[56] References Cited

FOREIGN PATENT DOCUMENTS

063879A2 11/1982 United Kingdom .

OTHER PUBLICATIONS

Herman et al., Chemical Abstracts, vol. 105, 111279d (1986).
Shimkus et al., Chemical Abstracts, vol. 105, 187048y (1986).
Langer, P. R. Waldrop, A. A. & Ward, D. C. (1981) *Proc. Natl. Acad. Sci. U.S.A.* 78, 6633–6637.
Shaw, B. R., Herman, T. M., Kovacic, R. T., Beaudreau, G. S. & Van Holde, K. E. (1976) *Proc. Natl. Acad. Sci. U.S.A.* 73, 505–509.
Rigby, P. W. J., Dieckmann, H., Rhodes, C. & Berg, P. (1977) *J. Mol. Biol.* 113, 237–251.
Penefsky, H. S. (1977) *J. Biol. Chem.* 252, 2891–2899.
Tatchell, K. & Van Holde, K. E. (1977) *Biochemistry* 16, 5295–5303.
Brigati, D. J., Myerson, D., Leary, J. J., Spalholz, B., Travis, S. Z., Fong, C. K. Y., Hsiung, G. D. & Ward, D. C. (1983) *Virology* 126, 32–50.
Singer, R. H. & Ward, D. C. (1982) *Proc. Natl. Acad. Sci. U.S.A.* 79, 7331–7335.
Cotton, R. W. & Hamkalo, B. A. (1981) *Nucleic Acids Res.* 9, 445–457.
Pierce Chemical Company, Dec. 1984 Publication.

*Primary Examiner*—J. R. Brown
*Assistant Examiner*—Jenny Tou
*Attorney, Agent, or Firm*—Quarles & Brady

[57] ABSTRACT

Novel biotinylated nucleotides have a chemically cleavable linker arm between a biotin and an organic basic group. They are useful in a method of isolating target macromolecules from crude physiological mixtures. The biotinylated nucleotides are bound via their organic basic groups to macromolecules having an affinity for the target macromolecules and brought into contact with the target macromolecules to form a biotinylated nucleotide-affinity macromolecule - target macromolecule complex. The complex thus obtained is brought into contact with immobilized avidin whereupon the biotin moeity binds to the avidin. The complex and avidin are washed to remove undesired substances and then the chemically cleavable bond in the nucleotide is cleaved to obtain the affinity-macromolecule - target macromolecule complex from which the target macromolecule can be obtained.

7 Claims, 1 Drawing Sheet

CHEMICALLY CLEAVABLE NUCLEOTIDES

FIELD OF THE INVENTION

The present invention relates generally to nucleotides. More particularly, it relates to chemically cleavable nucleotides useful as hybridization probes and in the isolation of target macromolecules from physiological mixtures.

BACKGROUND OF THE INVENTION

The detection of specific DNA sequences by hybridization probes containing biotinylated nucleotide analogs, which are described in European Patent Application No. 0063 879A2 filed Apr. 6, 1982, is proving to be a very useful alternative to traditional procedures utilizing radiolabeled probes. Because of the extremely high affinity of the glycoprotein avidin for biotin ($K_{dis}=10^{-15}M$), a detection system capable of detecting single copy mammalian DNA sequences has been developed based upon the formation of a ternary complex involving biotin, avidin and polymers of alkaline phosphatase. This highly sensitive detection system, coupled with other advantages of the biotin-avidin system such as probe stability (biotinylated DNA does not decay as does radiolabeled DNA) and the time required for detection (only 1 hr is required to visualize biotinylated DNA) promise to make the use of biotinylated DNA probes the method of choice in hybridization procedures in the very near future.

The highly specific and very strong binding of biotin to avidin ($K_D 10^{-15}M$) is the major reason that the avidin-biotin interaction is also gaining in popularity as a tool for isolating macromolecules from crude physiological mixtures. The strong avidin-biotin complex can provide a one step, high yield retrieval of target macromolecules as biotinylated macromolecules from crude physiological mixtures. Unfortunately, once isolated, biotinylated macromolecules cannot be gently released from the avidin so that the target macromolecule can be obtained. Dissociation of the avidin-biotin complex usually requires 6 molar guanidine HCl, pH 1.5, an environment too extreme for many macromolecules.

The use of the guanido analog of biotin, 2-iminobiotin, does satisfy the problem of reversible biotinylation to some extent because avidin binds to 2-iminobiotin tightly at pH values of 9.5 and higher and dissociates at pH values of 4 and lower. However, in addition to the pH limitations associated with its use, the avidin-iminobiotin interaction is not nearly as strong as that of avidin-biotin.

There is a need for a gentle, nondestructive method for isolating target macromolecules from crude physiological mixtures. Such a method could be a useful tool in the identification, purification and subsequent characterization of a number of biologically significant macromolecules, such as DNA-protein complexes.

SUMMARY OF THE PRESENT INVENTION

It is an object of the present invention to disclose a gentle nondestructive method for isolating target macromolecules from crude physiological mixtures which includes using novel nucleotides of the present invention and an avidin affinity column.

It is an object to disclose novel nucleotides with a chemically cleavable group which are useful in the above method and as hybridization probes.

Still further, it is an object to disclose novel chemically cleavable biotinylated nucleotides which contain a sulfur-sulfur linkage.

In addition it is an object to disclose novel biotin derivatives that are useful in preparing the nucleotides of the present invention.

The nucleotides of the present invention may be represented by the following generic formula:

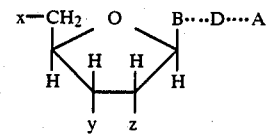

wherein B represents an organic basic group such as a purine, deazapurine, or pyrimidine moiety covalently bonded to the $C^{1'}$-position of the sugar moiety, provided that when B is purine or 7-deazapurine, it is attached at the $N^9$-position of the purine or deazapurine, and when B is pyrimidine, it is attached at the $N^1$-position;

wherein A represents a moiety consisting of at least three carbon atoms which is capable of forming a detectable complex with a polypeptide when the compound is incorporated into a double-stranded ribonucleic acid, deoxyribonucleic acid duplex, or DNA-RNA hybrid;

wherein the dotted line represents a 12 to 20 atom linker and D is a chemically cleavable bond, joining B and A, provided that if B is purine the linkage is attached to the 8-position of the purine, if B is 7-deazapurine, the linkage is attached to the 7-position of the deazapurine, and if B is pyrimidine, the linkage is attached to the 5-position of the pyrimidine; and wherein each of x, y, and z represents

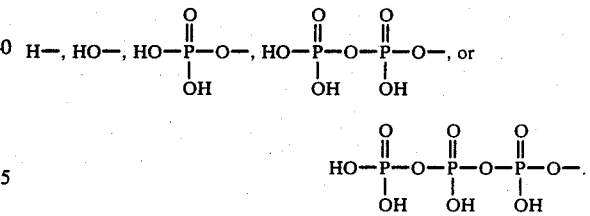

In addition to use as hybridization probes in the manner described in the aforementioned European patent, the novel biotinylated nucleotide analogs of the present invention may be used in a method of isolating specific macromolecules, such as DNA-protein complexes from crude physiological mixtures.

With prior art methods, a specific fragment of DNA could be affinity labeled with biotin and then introduced into a crude cell lysate which contains a number of proteins that normally bind tightly to that sequence of nucleotides. Following incubation, the biotinylated DNA with its found proteins could be isolated from the crude lysate by affinity chromatography on an avidin-agarose column. For example, those proteins that normally bind to DNA replication origins to initiate DNA replication can be both identified and purified in a single step by using a fragment of DNA known to contain an origin of DNA replication. However, it is at this point in the prior art procedure that a problem arises. The very feature of the biotin-avidin system that makes it so useful—i.e. the extremely high affinity of avidin for biotin—now becomes a problem in that it is now necessary to dissociate the biotin-avidin complex so that the purified biotinylated-DNA-protein complex can be recovered from the column and further characterized. Previous approaches to solve this problem—the use of iminobiotin in the nucleotide analog or the use of low affinity monomer avidin affinity columns—have not been satisfactory because the high affinity biotin-avidin interaction that is needed in the initial step is sacrificed in order to be able to dissociate the complex in the final step.

The advantages of the reversible biotinylation method are readily apparent. Macromolecules of interest can be fished out of complex physiological mixtures intact and under mild isolation conditions. The high affinity between avidin and biotin insures a high yield isolation while sensitive active sites on the target macromolecules are kept stabilized through binding to the affinity labelled DNA.

The novel method of the present method can be used to isolate specific DNA-protein complexes by incorporating a nucleotide of the present invention into the DNA (e.g., by *E. coli* polymerase I in a standard nick-translation reaction), binding the nucleotide DNA to an avidin-agarose affinity column and then recovering the specific nucleotide DNA minus the biotin moeity from the column by cleaving the chemically cleavable bond in the linker chain of the biotinylated nucleotide.

Particularly useful in the method of the present invention are compounds encompassed by formula I in which A is non-aromatic; A is at least $C_5$; the chemical linkage joining B and A is 12 or 19 atoms and D is a chemically clearable disulfide bond; A is biotin or iminobiotin; and B is a pyrimidine or 7-deazapurine. These compounds may be prepared by a process which involves:

(a) reacting a compound having the structure:

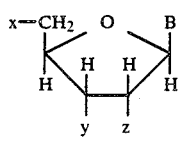

with a mercuric salt in a suitable solvent under suitable conditions so as to form a mercurated compound having the structure:

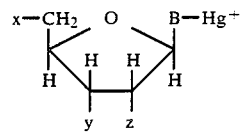

(b) reacting said mercurated compound with a chemical moiety reactive with the $-Hg^+$ portion of said mercurated compound and represented by the formula $\cdot\cdot D^N \ldots$, said reaction being carried out in an aqueous solvent and in the presence of $K_2PdCl_4$ under suitable conditions so as to form a compound having the structure:

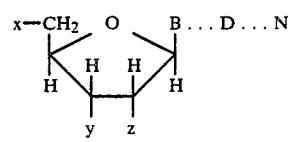

wherein N is a reactive terminal functional group or is A; and (c) recovering said compound as said modified nucleotide when N is A, or when N is a reactive terminal group, reacting said compound with a compound having the structure M—A, wherein M represents a functional group reactive with N in an aqueous solvent under suitable conditions so as to form said modified nucleotide, which is then recovered.

Especially useful in the preparation of the nucleotide of the present invention are biotin derivatives of the following fomula:

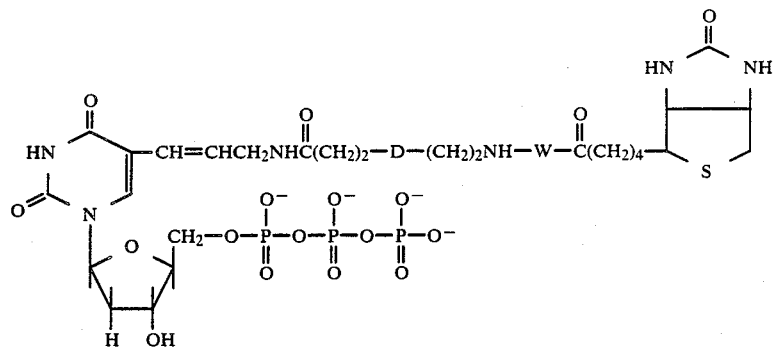

in which D is a disulfide linkage and W is a single bond or

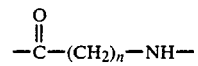

in which n is 2 to 6.

The preparation of a specific preferred nucleotide of the present invention may be illustrated as follows:

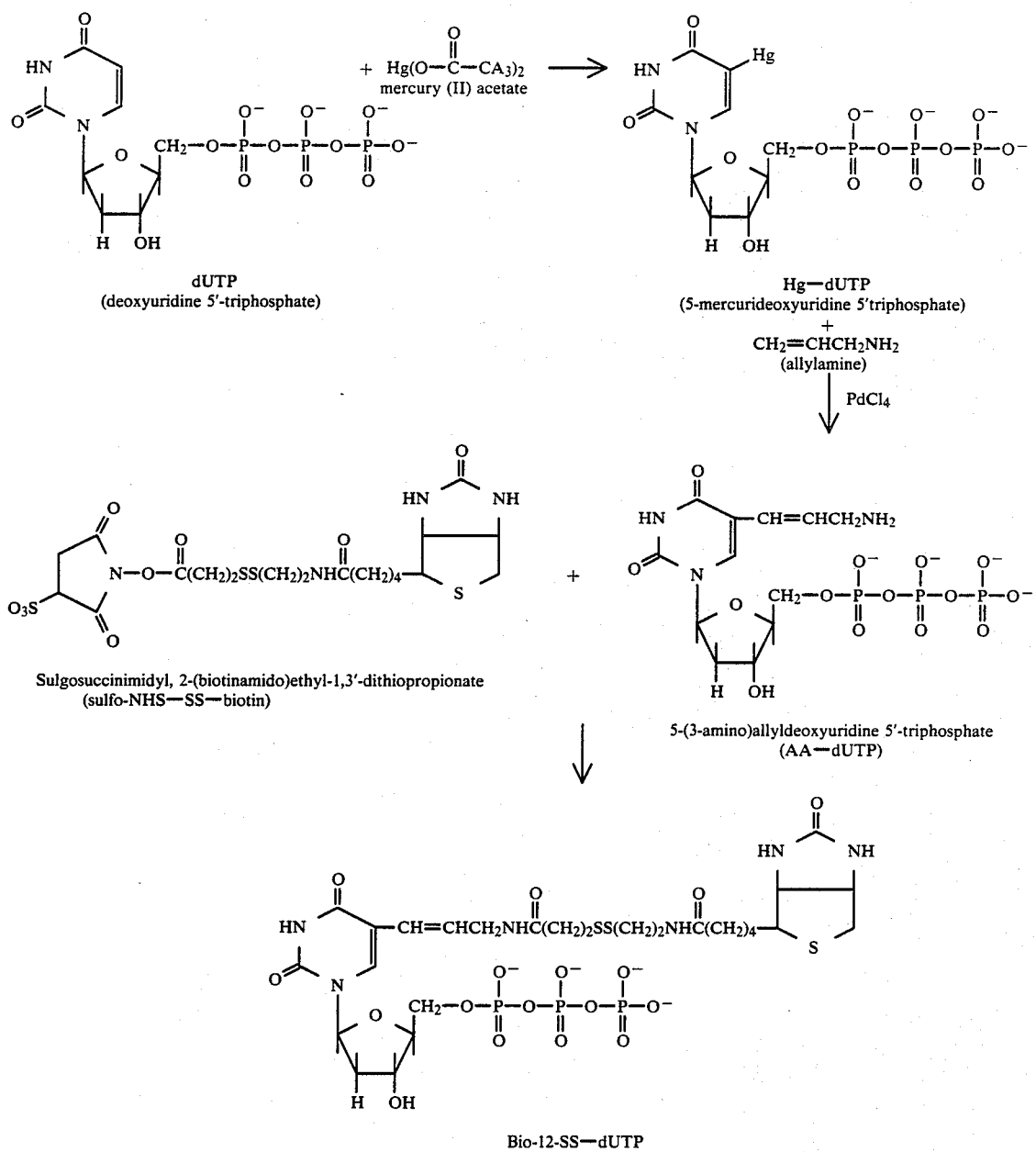

DESCRIPTION OF THE PREFERRED EMBODIMENT

Figure 1:
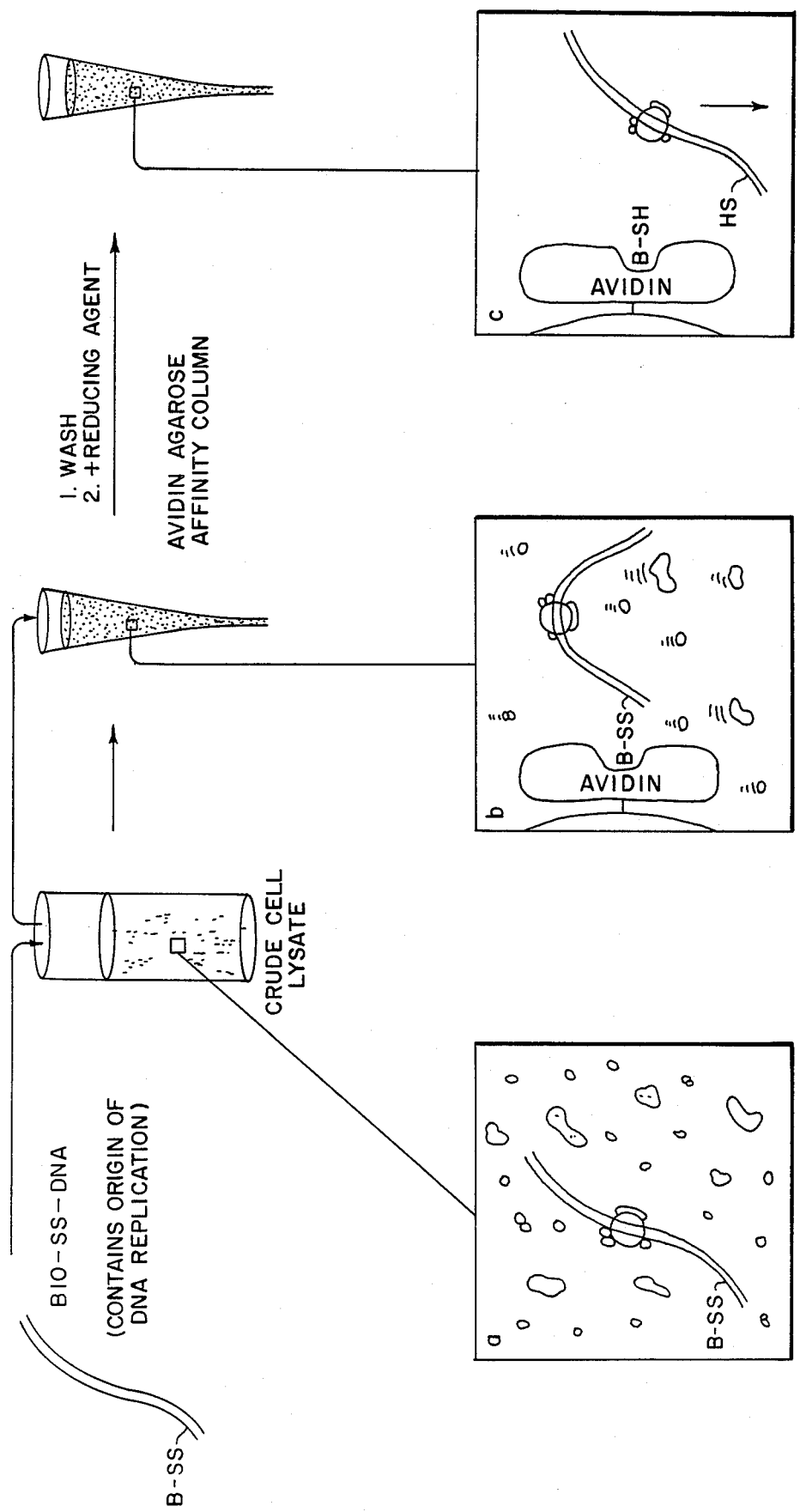
FIG. 1 is a schematic illustration of the use of the method and a nucleotide of the present invention to isolate a DNA-replication complex.

In the preferred embodiment the chemically cleavable nucleotides of the present invention have the following formula:

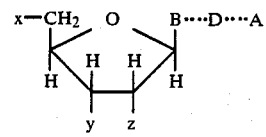

in which x, y and z are as previously defined, A is biotin, B is a pyrimidine, ···D··· is 12 to 20 atoms and D is a disulfide linkage.

Preferred biotin deviatives useful in preparing the chemically cleavable nucleotide are compounds of the formula:

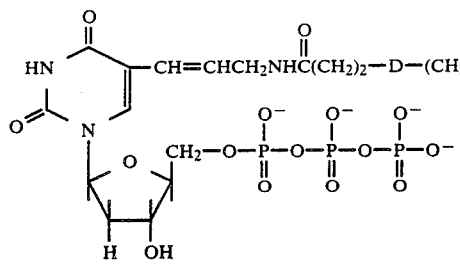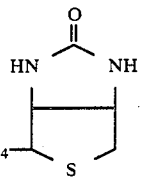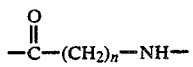

in which W is a single bond or $$-\overset{O}{\underset{\|}{C}}-(CH_2)_n-NH-$$

and n is 2 to 6. Derivatives in which W is between D and the pyrimidine base also may be used.

The practice of the invention is further illustrated by the examples which follow in which Bio-12SS-dUTP is a biotin derivative containing a disulfide bond in the 12-atom linker joining biotin to the C-5 of the pyrimidine ring; Bio-4-dUTP and Bio-11-dUTP are analogs of UTP that contain a biotin molecule linked to the C-5 position of the pyrimidine ring through linker arms that are 4 and 11 atoms long; AA-dUTP is 5-(3-amino) allyldeoxyuridine 5'-triphosphate and sulfo-NHS-SS-biotin is sulfosuccinimidyl, 2-(biotinamido) ethyl-1,3'-dithiopropionate.

The method of isolating a DNA-replication complex using the nucleotides of the present invention is illustrated in FIG. 1. As seen therein, a fragment of DNA that is known to contain an origin of DNA replication is end-labeled with Bio-SS-dUTP. The biotinylated DNA is then added to a heterogeneous mixture of proteins including several which specifically bind the nucleotide sequence comprising the origin of replication (Step a). After incubation, the mixture is applied to an avidin-agarose affinity column. The Bio-SS-DNA and its bound proteins will bind to the column while all unbound proteins will be washed free (Step b). Subsequent washing of the column with buffer containing a reducing agent such as DTT will release the DNA-protein complex which can then be further characterized (Step c).

MATERIALS AND METHODS

Materials. Deoxyuridine 5'-triphosphate (dUTP) was purchased from Sigma. Allylamine was obtained from Aldrich. Radiolabeled nucleotides were purchased from Amersham ([$^3$H]dTTP) and New England Nuclear ([$^{32}$P]dCTP). Sulfosuccinimidyl, 2-(biotinamido)ethyl-1,3'-dithiopropionate (sulfo-NHS-SS-biotin) is available from Pierce Chemical. The dUTP analog Bio-11-dUTP (analog that contains a biotin molecule linked to the C-5 position of the pyrimidine ring through a linker arm 11 atoms long) was purchased from Enzo Biochemicals (New York). *Escherichia coli* DNA polymerase I was obtained from New England Biolabs.

Synthesis of Bio-SS-dUTP. Bio-SS-dUTP was synthesized and purified by a modification of the procedure described by Langer et al. (1). Briefly, beginning with 50 mg of dUTP, 5-(3-amino)allyldeoxyuridine 5'-triphosphate (AA-dUTP) was synthesized and purified by chromatography on DEAE-Sephadex A-25 as described (1). Column fractions containing AA-dUTP, identifiable by its unique absorbance spectrum ($\lambda_{max}$ at 289 nm and 240 nm; $\lambda_{min}$ at 262 nm), were pooled and AA-dUTP was precipitated by the addition of 3 vol of cold, absolute ethanol. From 90 μmol of dUTP, 18 μmol of AA-dUTP can be obtained.

It was not necessary to further purify the AA-dUTP by HPLC at this stage in the synthesis. Instead, 2.0 μmol of AA-dUTP in 200 μl of 0.1 M sodium borate (pH 8.5) was added directly to 2.0 μmol of sulfo-NHS-SS-biotin. The reaction was allowed to proceed at room temperature for 1 to 2 hr. The resulting Bio-SS-dUTP was purified by ion-pair reversed-phase HPLC using a Bio-Sil ODS-5S column (250×4 mm; Bio-Rad). Aliquots of the reaction (100 μl) were adjusted to 50 mM Et$_3$NHCO$_3$ (pH 7.5) and 10% acetonitrile, diluted to 500 μl with the same buffer, and applied to the column at a flow rate of 0.5 ml/min (1600 psi). Bio-SS-dUTP was eluted isocratically with 50 mM Et$_3$NHCO$_3$ (pH 7.5) and 10% acetonitrile. Column fractions containing Bio-SS-dUTP were pooled, rotary evaporated, resuspended in 10 mM Tris HCl (pH 7.5); and stored at −80° C. From 2.0 μmol of AA-dUTP, 1.0–1.6 μmol of Bio-SS-dUTP can be obtained by this procedure.

Nick-Translation Reactions. Nucleosome length DNA fragments [145 base pairs (bp)] were purified from monomer nucleosomes prepared by micrococcal nuclease digestion of chicken erythrocyte nuclei followed by fractionation on an agarose A-5m column (2). Four microgram aliquots of 145-bp DNA fragments in 0.1 ml of 50 mM Tris-HCl, pH 7.5/5 mM MgCl$_2$/50 μg of bovine serum albumin per ml were nicktranslated (3) in the presence of 20 μM dATP and dGTP, 20 μM [$^{32}$P]dCTP (2-5 μCi/nmol; 1 Ci =37 GBq), and either dTTP, Bio-4-dUTP, or Bio-SS-dUTP as indicated. 2-Mercaptoethanol was eliminated from the nick-translation buffer to preserve the Bio-SS-dUTP. DNase I (0.01 ng per 0.1 ml of reaction mixture) was added to the reaction, which was then incubated for 5 min at 15° C. prior to the addition of *E. coli* DNA polymerase I (4 units per 0.1 ml of reaction mixture).

When the nick-translated DNA was to be used in either affinity chromatography studies or in nucleosome reconstitution reactions, it was separated from unincorporated nucleotides by chromatography through spin columns (4) of Sephadex G-50 in 10 mM Tris HCl, pH 7.5/1 mM EDTA/50 mM NaCl.

Avidin-Agarose Chromatography. Affinity columns were constructed in 200 μl pipette tips (Gilson) plugged with glass wool. One hundred microliters of a 50% slurry of avidin-D-agarose (Vector Laboratories, Burlingame, CA) was added to each column and washed 3 times with 200-μl aliquots of 10 mM Tris-HCl, pH 7.5/1 mM EDTA/50 mM NaCl. Each 200-μl aliquot was gently forced through the column in 15 sec by air pressure. DNA samples containing 0.1–0.2 μg of nick-translated DNA in 200 μl of the same buffer were applied and forced through the column as described for the washing step. The 200-μl flow-through aliquot was reapplied to the column one time. After the last wash, the column was inverted in a scintillation vial, which was then centrifuged to remove the resin from the column. Scintillation fluid was added directly to the resin and radioactivity was measured.

It should be noted that nonbiotinylated DNA binds nonspecifically to avidin-agarose in the presence of 50 mM NaCl. However, increasing the NaCl concentration to 200 mM effectively eliminates this low-affinity binding with no effect on the binding of biotinylated DNA to the column.

To determine whether biotinylated nucleosomes could be selectively bound to and eluted from avidin-agarose, aliquots of sucrose gradient fractions containing 1–2 μg of reconstituted 11S nucleosomes were applied directly to avidin-agarose columns and washed as described for DNA samples. When the Bio-SS-nucleosomes recovered from avidin-agarose were to be reanalyzed by sedimentation in a second sucrose gradient, 50 g of unlabeled monomer nucleosomes was added to each dithiothreitol-containing wash immediately after its elution from the avidin-agarose column. This addition of excess unlabeled nucleosomes was necessary to stabilize the recovered Bio-SS-nucleosomes that would have otherwise dissociated because of their low concentration.

Reconstitution of Biotinylated Nucleosomes. Reconstitution of nucleosomes containing biotinylated DNA was done by the step-dialysis procedure described by Tatchel and Van Holde (5). Two micrograms of nick-translated 145-bp DNA fragments was mixed with 20 g of unlabeled monomer nucleosomes (2) in a total volume of 0.4 ml of 10 mM Tris HCl, pH 7.5/1 mM EDTA/2.0 M NaCl. After dialysis, the reconstitution mixture was then layered on a 5%–20% neutral sucrose gradient in 10 mM Tris HCl, pH 7.5/1 mM EDTA/0.05 M NaCl and centrifuged at 5° C for 15 hr at 35,000 rpm in an SW41 rotor. The radioactivity present in aliquots of each fraction was measured to establish the sedimentation profile of each reconstitution mixture. As a control, authentic 11S monomer nucleosomes were sedimented in a parallel gradient and were detected by measuring the absorbance (260 nm) of each fraction.

RESULTS

Synthesis of Bio-SS-dUTP. Bio-SS-dUTP, a chemically cleavable biotinylated nucleotide by virtue of the disulfide bond contained in the linker arm that joins biotin to the C-5 of the pyrimidine ring, has been synthesized. Its synthesis followed closely the procedure originally described by Langer et al. (1) for the synthesis of Bio-4-dUTP. The reaction between sulfo-NHSS-SS-biotin and AA-dUTP proceeded quickly with 50%–80% of the AA-dUTP being converted to Bio-SS-dUTP. Bio-SS-dUTP was purified from the reaction by ion-pair reversed-phase HPLC. Under the conditions described, Bio-SS-dUTP eluted from the column with a retention time of 22 min (flow rate, 0.5 ml/min), immediately after two minor (about 1%) reaction products.

The presence of a chemically cleavable disulfide bond in the Bio-SS-dUTP was demonstrated by its chromatography in presence of 2-mercaptoethanol. An identical aliquot of the Bio-SS-dUTP reaction was supplemented with 2-mercaptoethanol to a final concentration of 5 mM immediately prior to its application and chromatography on HPLC. As expected, no UV-absorbing material eluted from the column with the retention time expected for intact Bio-SS-dUTP. Instead, there was a corresponding increase in the material eluting from the column with the solvent breakthrough (3.3 min). Since AA-dUTP elutes from this column with the breakthrough, and Bio-4-dUTP has a retention time of 5.7 min, the nucleotide-containing product of disulfide cleavage of Bio-SS-dUTP would be expected to elute with or near the breakthrough volume.

Bio-SS-dUTP Is a Substrate for *E. coli* DNA Polymerase. To determine whether Bio-SS-dUTP could serve as a substrate for *E. coli* DNA polymerase I, its incorporation into DNA in a nick-translation reaction was measured. The incorporation of [$^{32}$P]dCTP into purified nucleosome-length DNA fragments (145 bp) in the presence of 20 μM dATP, dGTP, dCTP, and either the normal nucleotide, TTP, or one of three biotinylated nucleotide analogs was measured. Bio-SS-dUTP was capable of supporting the nick-translation reaction at 35%–40% the rate observed with an equal concentration of TTP. Bio-11-dUTP was similar to Bio-SS-dUTP, while the smaller biotinylated nucleotide analog, Bio-4-dUTP, supported the reaction at a rate 60% that observed for TTP. Therefore, just as was reported earlier for Bio-4-dUTP and Bio-11-dUTP (1, 6) Bio-SS-dUTP is a good substrate for *E. coli* DNA polymerase. If no TTP is present with the biotinylated nucleotides in the nick-translation reaction, the newly synthesized DNA is very heavily biotinylated. To reduce this level of modification, the nick-translation reactions can be performed in the presence of μM/10TTP/10 μM Bio-SS-dUTP. Under these conditions, the reaction proceeds at a rate only slightly slower than in the presence of 20 μM TTP alone, and the resulting DNA contains sufficient biotinylated nucleotides to bind to an avidin-agarose affinity column.

Bio-SS-DNA Can Be Recovered from an Avidin-Agarose Affinity Column. Having established that Bio-SS-dUTP could be incorporated into DNA by nick-translation, we next asked whether (i) the biotinylated DNA could be bound to a avidin-agarose affinity column and (ii) the bound DNA could be recovered from the column after reduction of the disulfide bond in the linker arm by dithiothreitol. Two controls were included. First, nonbiotinylated DNA, nick-translated in the presence of [$^3$H]TTP (no biotinylated nucleotide), was mixed with $^{32}$P-labeled biotinylated DNA to demonstrate the initial selective binding of the biotinylated DNA to the affinity column. Second, the recovery of $^{32}$P-labeled Bio-SS-DNA from the column was compared with that of DNA containing a noncleavable biotinylated nucleotide, $^{32}$P-labeled Bio-4-dUTP.

Both $^{32}$P-labeled Bio-4-DNA and $^{32}$P-labeled Bio-SS-DNA were selectively bound to the avidin-agarose columns. Whereas 98% of the $^3$H-labeled DNA was recovered from the columns after washing with 200 mM NaCl, 95% of the biotinylated DNA (both $^{32}$P-labeled Bio-4-DNA and $^{32}$P-labeled Bio-SS-DNA) remained bound under these conditions. The addition of 50 mM dithiothreitol to the elution buffer failed to remove any of the bound $^{32}$P-labeled Bio-4-DNA. As expected, 95% of the $^{32}$P-labeled Bio-4-DNA was found still bound to the avidin-agarose resin at the end of the experiment. It should be noted that previous attempts to remove the DNA probe Bio-4-DNA from avidin-agarose columns in our laboratory as well as others (1) by washing with buffers containing 1.0 M NaCl, 8 M urea or 2 mM biotin have been unsuccessful. Therefore, $^{32}$P-labeled Bio-4-DNA is irreversibly bound to avidin-agarose. In contrast five consecutive washes of the column containing 1 bound $^{32}$P-labeled Bio-SS-DNA with buffer containing 50 mM dithiothreitol resulted in the recovery of a total of 87% of the DNA from the affinity column. Only 7.3% of the $^{32}$P-labeled Bio-SS-DNA remained bound to the resin. Thus, Bio-SS-dUTP functions as a chemically cleavable nucleotide analog that can be used to initiallly bind biotinylated DNA to an avidin-agarose affinity column and subsequently release that DNA when its linker arm is broken by a reducing agent.

Biotinylated Nucleosomes Can Be Selectively Bound to and Recovered from Avidin-Agarose. The initial interest in biotinylated nucleotides resulted from their potential usefulness in affinity labeling newly replicated DNA. If the newly biotinylated DNA was assembled into nucleosomes, it was reasoned that it might be possible to isolate the newly formed DNA-protein complexes by avidin-agarose chromatography and then recover the intact complex for further analysis. To test the feasibility of such an approach, we first asked whether biotinylated DNA could be assembled into the characteristic 11S nucleosome in an in vitro nucleosome reconstitution reaction. Nucleosome-length fragments of DNA were nick-translated in the presence of [$^{32}$P]dCTP and either 20 $\mu$M mixture of 10 $\mu$M TTP and 10 $\mu$M Bio-4-dUTP, or a mixture of 10 $\mu$M TTP and 10 $\mu$M Bio-SS-dUTP. The labeled DNA was then added to a 10-fold excess of nonlabeled monomer nucleosomes. NaCl was added to the mixture to a final concentration of 2.0 M to dissociate the nucelosomes into their DNA and histone components (5). The mixture was then dialyzed in a step-wise fashion into a buffer containing 50 mM NaCl. To assess how effectively the biotinylated DNA fragments had competed for the available histone octamers during the dialysis, the reconstitution mixtures were sedimented in neutral sucrose gradients. Both biotinylated DNAs were capable of interacting with histone octamers to form an 11S nucleosome in yields comparable to that observed for the nonbiotinylated nick-translated DNA. Between 40% and 60% of the biotinylated DNA has been routinely found assembled into 11S nucleosomes in this type of experiment. The reconstituted material sedimenting ahead of the 11S monomer nucleosomes can be attributed to the presence of histone H1 and DNA fragments 145 bp in the preparation of nucleosomes used in this experiment.

To determine whether the biotinylated nucleosomes could be bound to and recovered from avidin-agarose as was previously shown for biotinylated DNA, aliquots of the sucrose gradient fractions containing reconstituted 11S nucleosomes were applied directly to avidin-agarose columns. The nonbiotinylated and biotinylated nucleosomes behaved in the same way as their DNA counterparts, although a somewhat higher level of nonbiotinylated nucleosomes remained bound to the avidin-agarose after extensive washing. It should be possible to eliminate the nonspecifically bound nucleosomes by use of a streptavidin affinity column (6). The concentration of dithiothreitol used to elute the Bio-SS-nucleosomes was 500 mM in the foregoing experiment. However, other experiments have shown that 50 mM dithiothreitol results in the recovery of the same percent of Bio-SS-nucleosomes.

Finally, to demonstrate that the recovered Bio-SS-nucleosomes were intact 11S particles, they were sedimented a second time in a sucrose gradient. Eighty percent of the recovered $^{32}$P-labeled Bio-SS-nucleosomes cosedimented with authentic 11S monomeric nucleosomes. The small amount of dissociation that was observed (20%) can be attributed to the normal dissociation of purified monomer nucleosomes in solution at concentrations $>20$ $\mu$g/ml (7).

DISCUSSION

We have described the synthesis and one specific application of Bio-SS-dUTP, a biotinylated nucleotide analog containing a chemically cleavable disulfide bond in the linker arm joining biotin to dUTP. The properties of Bio-SS-dUTP are similar to those of Bio-4-dUTP and Bio-11-dUTP in terms of its incorporation into DNA by nick-translation and the subsequent binding of the biotinylated DNA to an avidin-agarose affinity column. However, the presence of the disulfide group in the linker of Bio-SS-dUTP provides a means to recover the Bio-SS-DNA from an avidin-agarose column. Approximately 90% of the bound Bio-SS-DNA was recovered by washing the column with buffer containing 50 mM dithiothreitol. This approach to recovering biotinylated DNA from an avidin affinity column is superior to other approaches, such as the use of low affinity monomer avidin columns or of iminobiotin-labeled DNA. In our procedure, the high affinity of avidin for biotin can be exploited fully while allowing for recovery of DNA by a mild nondenaturing treatment.

The ability to cleave the linker between biotin and dUTP under mild nondenaturing conditions makes it possible to isolate intact protein-Bio-SS-DNA complexes by avidin-agarose chromatography. As a demonstration of such an application, we have shown that reconstituted nucleosomes containing Bio-SS-DNA can be specifically bound to and subsequently recovered from an avidin-agarose column. The Bio-SS-DNA used for nucleosome reconstitution was nick-translated in the presence of equal concentrations of TTP and Bio-SS-dUTP. In this way, the incorporation of Bio-SS-dUTP into DNA was limited to 2–5 residues per nucleosome-length fragment. Bio-SS-DNA prepared in this way was reconstituted into nucleosomes with the same efficiency as nick-translated nonbiotinylated DNA. At the same time, the binding of the Bio-SS-nucleosomes to avidin-agarose was both highly selective and sensitive. We have observed that biotinylated nucleosomes are quantitatively bound to avidin-agarose even when mixed with a 10,000-fold excess of nonbiotinylated nucleosomes (data not shown). Most importantly, Bio-SS-nucleosomes were recovered from the affinity column as intact 11S nucleosomes as judged by velocity sedimentation in neutral sucrose gradients.

Many areas of research in molecular biology are concerned with the identification and isolation of proteins or protein complexes that bind in a sequence-specific manner to DNA. It is possible to isolate these proteins by affinity chromatography after their binding to specific Bio-SS-labeled DNA fragments. Most importantly, in addition to the isolation and subsequent identification of these proteins, this approach provides a means to recover the complexes in their native form. These complexes can then be further analyzed with respect to both the specific protein-protein and protein-DNA interactions that may be present. Specific examples of areas in which this approach is useful include the deposition of pre-existing or new histones at DNA replication forks, the identification of specific transcription factors, and the isolation of hormone-receptor-DNA complexes.

The above experimental work describes the preparation of a biotinylated nucleotide analog containing a disulfide bond in a 12-atom linker joining biotin to the C-5 of the pyrimidine ring. It will be appreciated by those skilled in the art that nucleotides having linkers of more or less than 12 atoms and other types of chemically cleavable bonds may be prepared in an analogous manner. For example, the chemically cleavable bond could be a phenyl ester bond cleavable by hydroxylamine. In addition, it should be understood that although the use of avidin has been described, streptavidin or other functionally equivalent materials may be used.

It is to be understood that the foregoing description has been for purposes of illustration and that the invention is not to be limited except by the claims.

REFERENCES

1. Langer, P. R., Waldrop, A. A. & Ward, D. C. (1981) Proc. Natl. Acad. Sci. USA 78, 6633-6637.
2. Shaw, B. R., Herman, T. M., Kovacic, R. T., Beaudreau, G. S. & Van Holde, K. E. (1976) Proc. Natl. Acad. Sci. USA 73, 505-509.
3. Rigby, P. W. J., Dieckmann, H., Rhodes, C. & Berg, P. (1977) J. Mol. Biol. 113, 237-251.
4. Penefsky, H. S. (1977) J. Biol. Chem. 252, 2891-2899.
5. Tatchell, K. & Van Holde, K. E. (1977) Biochemistry 16, 5295-5303.
6. Brigati, D. J., Myerson, D., Leary, J. J., Spalholz, B., Travis, S. Z., Fong, C. K. Y., Hsiung, G. D. & Ward, D. C. (1983) Virology 126, 32-50.
7. Singer, R. H. & Ward, D. C. (1982) Proc. Natl. Acad. Sci. USA 79, 7331-7335.
8. Cotton, R. W. & Hamkalo, B. A. (1981) Nucleic Acids Res. 9, 445-457.

I claim:

1. A compound having the structure:

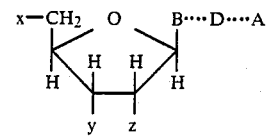

wherein

B is selected from purine, 7-deazapurine and pyrimidine provided that when B is purine or 7-deazapurine, it is attached at the $N^9$-position of purine or deazapurine, and when B is pyrimidine, it is attached at the $N^1$-position; wherein A represents biotin or iminobiotin wherein ...D... is selected from the formulae:

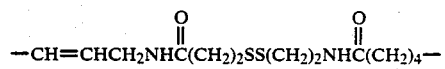

and

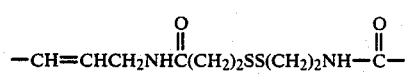

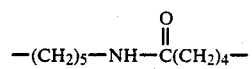

D is a chemically cleavable disulfide bond and ...D... joins B and A, provided that if B is purine, the linkage is attached to the 8-position of the purine, if B is 7-deazapurine, the linkage is attached to the 7-position of the deazapurine, and if B is pyrimidine, the linkage is attached to the 5-position of the pyrimidine; and wherein each of x, y and z represents

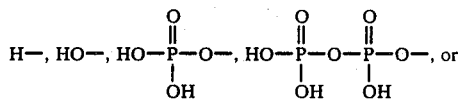

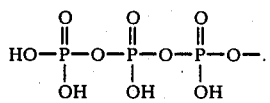

2. A compound in accordance with claim 1 wherein A is biotin.

3. A compound in accordance with claim 1 wherein A is iminobiotin.

4. A compound in accordance with claim 1 wherein B is purine, deazapurine, or pyrimidine.

5. A compound of the formula:

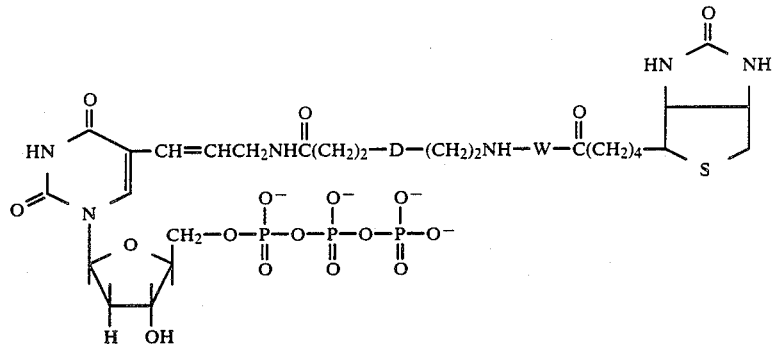
in which D is a chemically cleavable disulfide bond and W is a single bond or
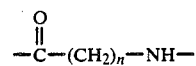
and n is 2 to 6.
6. A compound of the formula:
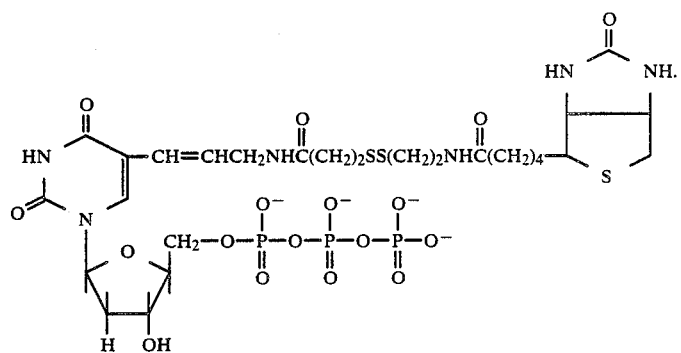
7. A compound of the formula:
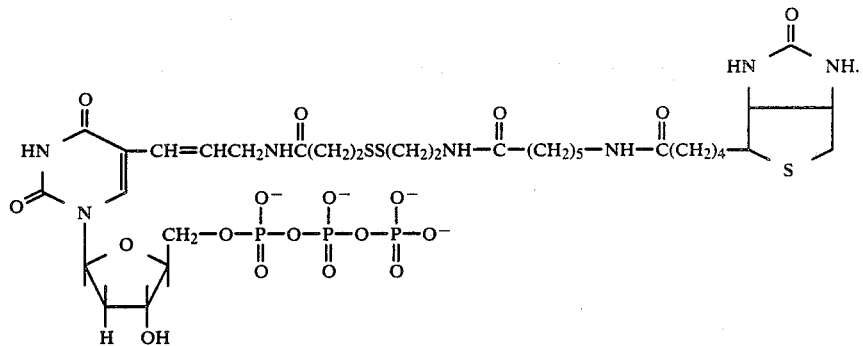
* * * * *